United States Patent
Wilkowske et al.

(10) Patent No.: US 10,493,708 B2
(45) Date of Patent: Dec. 3, 2019

(54) STEERABLE CATHETER AND METHODS OF MAKING THE SAME

(71) Applicant: St. Jude Medical, Atrial Fibrillation Division, Inc., St. Paul, MN (US)

(72) Inventors: Eric John Wilkowske, North Oaks, MN (US); Allan Manuel Fuentes, Mound, MN (US); Xiaoping Guo, Eden Prairie, MN (US); Xuan Yen Khieu, Maple Grove, MN (US); Linda Kay Nemec, Andover, MN (US); Richard E. Stehr, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1236 days.

(21) Appl. No.: 13/625,053

(22) Filed: Sep. 24, 2012

(65) Prior Publication Data
US 2013/0300036 A1    Nov. 14, 2013

Related U.S. Application Data

(63) Continuation of application No. 11/033,098, filed on Jan. 10, 2005, now Pat. No. 8,273,285.

(51) Int. Cl.
*A61M 25/00* (2006.01)
*B29D 23/00* (2006.01)
*A61M 25/01* (2006.01)

(52) U.S. Cl.
CPC .......... *B29D 23/00* (2013.01); *A61M 25/0012* (2013.01); *A61M 25/0045* (2013.01); *A61M 25/0147* (2013.01); *A61M 25/005* (2013.01)

(58) Field of Classification Search
CPC .......... A61M 25/0026; A61M 25/0028–0032; A61M 25/0043; A61M 25/005;
(Continued)

(56) References Cited

U.S. PATENT DOCUMENTS 3,293,351 A * 12/1966 Giaro ................... H01B 9/0611
                                                     174/105 R
4,934,049 A    6/1990 Kiekhafer et al.
(Continued)

FOREIGN PATENT DOCUMENTS

| EP | 1205208  | 5/2002  |
|----|----------|---------|
| GB | 1170018  | 11/1969 |
| JP | 54-12846 | 1/1979  |

*Primary Examiner* — Devin B Henson
*Assistant Examiner* — H. Q. Nguyen
(74) *Attorney, Agent, or Firm* — Wiley Rein LLP

(57) ABSTRACT

A method of manufacturing a flexible tubular body for a medical device includes extruding an inner layer from a thermoplastic polymer, pulling it over a mandrel, and tightening it down. If wire lumens were not formed in the inner layer when extruded, polymer spaghetti tubes with wire lumens are laid along the outer surface of the inner layer. Deflection wires are fed into the wire lumens. A wire braid is placed over the inner layer (and spaghetti tubes, if present) and tightened down. The components are encased in an outer polymer layer and a heat shrinkable tube. Pressurized fluid is injected into each wire lumen to maintain the internal diameter thereof greater than the diameter of the deflection wire received therein. Heat is applied to the assembled components, causing the layers to laminate. Once the laminated body has cooled, the heat-shrinkable tube is removed.

20 Claims, 3 Drawing Sheets

(58) Field of Classification Search
CPC .......... A61M 25/0052–0054; A61M 25/0133;
A61M 25/0147; A61M 25/0152; A61M
25/0009; A61M 25/0013; A61M 25/0015;
A61B 18/14; A61B 18/1492; A61B
18/24–245
See application file for complete search history.

(56) References Cited

U.S. PATENT DOCUMENTS

| | | | |
|---|---|---|---|
| 4,960,134 A | 10/1990 | Webster, Jr. | |
| 5,047,026 A | 9/1991 | Rydell | |
| 5,125,896 A | 6/1992 | Hojeibane | |
| 5,125,985 A | 6/1992 | Buchbinder et al. | |
| 5,269,757 A | 12/1993 | Fagan | |
| 5,277,199 A | 1/1994 | DuBois et al. | |
| 5,318,525 A | 6/1994 | West et al. | |
| 5,327,889 A | 7/1994 | Imran | |
| 5,327,906 A | 7/1994 | Fideler et al. | |
| 5,342,301 A | 8/1994 | Saab | |
| 5,354,297 A | 10/1994 | Avitall | |
| 5,364,351 A | 11/1994 | Heinzelman et al. | |
| 5,383,923 A | 1/1995 | Webster, Jr. | |
| 5,389,073 A | 2/1995 | Imran | |
| 5,391,147 A | 2/1995 | Imran et al. | |
| 5,395,328 A | 3/1995 | Ockuly et al. | |
| 5,395,329 A | 3/1995 | Fleischhacker et al. | |
| 5,397,304 A | 3/1995 | Truckai | |
| 5,423,772 A | 6/1995 | Lurie et al. | |
| 5,427,119 A | 6/1995 | Swartz et al. | |
| 5,431,168 A | 7/1995 | Webster, Jr. | |
| 5,445,148 A | 8/1995 | Jaraczewski et al. | |
| 5,478,330 A | 12/1995 | Imran et al. | |
| 5,487,757 A | 1/1996 | Truckai | |
| 5,497,774 A | 3/1996 | Swartz et al. | |
| 5,487,385 A | 7/1996 | Avitall | |
| 5,533,967 A | 7/1996 | Imran | |
| 5,545,200 A | 8/1996 | West et al. | |
| 5,549,581 A | 8/1996 | Lurie et al. | |
| 5,564,440 A | 10/1996 | Swartz et al. | |
| 5,575,766 A | 11/1996 | Swartz et al. | |
| 5,588,964 A | 12/1996 | Imran et al. | |
| 5,611,777 A | 3/1997 | Bowden et al. | |
| 5,628,316 A | 5/1997 | Swartz et al. | |
| 5,640,955 A | 6/1997 | Ockuly et al. | |
| 5,643,231 A | 7/1997 | Lurie et al. | |
| 5,656,028 A | 8/1997 | Swartz et al. | |
| 5,656,029 A | 8/1997 | Imran et al. | |
| 5,656,030 A | 8/1997 | Hunjan et al. | |
| 5,662,608 A | 9/1997 | Imran et al. | |
| 5,676,653 A * | 10/1997 | Taylor ............... | A61M 25/0147 604/523 |
| 5,690,611 A | 11/1997 | Swartz et al. | |
| 5,715,818 A | 2/1998 | Swartz et al. | |
| 5,722,963 A | 3/1998 | Lurie et al. | |
| 5,725,512 A | 3/1998 | Swartz et al. | |
| 5,779,669 A | 7/1998 | Haissaguerre et al. | |
| 5,800,413 A | 9/1998 | Swartz et al. | |
| 5,810,730 A | 9/1998 | Swartz et al. | |
| 5,814,027 A | 9/1998 | Hassett et al. | |
| 5,814,028 A | 9/1998 | Swartz et al. | |
| 5,814,029 A | 9/1998 | Hassett | |
| 5,827,278 A | 10/1998 | Webster | |
| 5,833,673 A | 11/1998 | Ockuly et al. | |
| 5,836,947 A | 11/1998 | Fleischman et al. | |
| 5,840,027 A | 11/1998 | Swartz et al. | |
| 5,842,984 A | 12/1998 | Avitall | |
| 5,843,031 A | 12/1998 | Hermann et al. | |
| 5,843,076 A | 12/1998 | Webster, Jr. et al. | |
| 5,846,223 A | 12/1998 | Swartz et al. | |
| 5,861,024 A | 1/1999 | Rashidi et al. | |
| 5,868,733 A | 2/1999 | Ockuly et al. | |
| 5,879,296 A | 3/1999 | Ockuly et al. | |
| 5,885,278 A | 3/1999 | Fleischman et al. | |
| 5,897,529 A | 4/1999 | Ponzi | |
| 5,902,289 A | 5/1999 | Swartz et al. | |
| 5,916,213 A | 6/1999 | Haissaguerre et al. | |
| 5,916,214 A | 6/1999 | Cosio et al. | |
| 5,921,924 A | 7/1999 | Avitall | |
| 5,921,957 A | 7/1999 | Killion et al. | |
| 5,931,811 A | 8/1999 | Haissaguerre et al. | |
| 5,944,690 A | 8/1999 | Falwell et al. | |
| 5,947,938 A | 9/1999 | Swartz et al. | |
| 5,993,462 A | 11/1999 | Pomeranz et al. | |
| 6,001,085 A | 12/1999 | Lurie et al. | |
| 6,002,955 A | 12/1999 | Willems et al. | |
| 6,022,341 A | 2/2000 | Lontz | |
| 6,024,722 A | 2/2000 | Rau et al. | |
| 6,030,371 A | 2/2000 | Pursley | |
| 6,033,403 A | 3/2000 | Tu et al. | |
| 6,048,329 A | 4/2000 | Thompson et al. | |
| 6,068,629 A | 5/2000 | Haissaguerre et al. | |
| 6,071,274 A | 6/2000 | Thompson et al. | |
| 6,090,084 A | 7/2000 | Hassett et al. | |
| 6,090,104 A | 7/2000 | Webster, Jr. | |
| 6,138,043 A | 10/2000 | Avitall | |
| 6,156,018 A | 12/2000 | Hassett | |
| 6,156,034 A | 12/2000 | Casio et al. | |
| 6,200,315 B1 | 3/2001 | Gaiser et al. | |
| 6,203,525 B1 | 3/2001 | Whayne et al. | |
| 6,203,531 B1 | 3/2001 | Ockuly et al. | |
| 6,219,582 B1 | 4/2001 | Hofstad et al. | |
| 6,241,754 B1 | 6/2001 | Swanson et al. | |
| 6,308,091 B1 | 10/2001 | Avitall | |
| 6,368,316 B1 * | 4/2002 | Jansen ............... | A61M 25/005 600/435 |
| 6,371,955 B1 | 4/2002 | Fuimaono et al. | |
| 6,447,507 B1 | 9/2002 | Bednarek et al. | |
| 6,450,948 B1 * | 9/2002 | Matsuura et al. ........... | 600/139 |
| 6,466,811 B1 | 10/2002 | Hassett | |
| 6,526,302 B2 | 2/2003 | Hassett | |
| 6,540,755 B2 | 4/2003 | Ockuly et al. | |
| 6,582,536 B2 | 6/2003 | Shimada | |
| 6,623,424 B2 | 9/2003 | Hayakawa et al. | |
| 6,709,455 B1 | 3/2004 | Chouinard et al. | |
| 6,913,617 B1 | 7/2005 | Reiss | |
| 6,926,669 B1 * | 8/2005 | Stewart et al. ............... | 600/439 |
| 6,951,554 B2 | 10/2005 | Johansen et al. | |
| 2002/0198492 A1 * | 12/2002 | Miller et al. ............... | 604/96.01 |
| 2004/0116848 A1 * | 6/2004 | Gardeski ........... | A61M 25/0147 604/95.01 |
| 2004/0122360 A1 * | 6/2004 | Waldhauser et al. ....... | 604/95.04 |
| 2005/0049574 A1 * | 3/2005 | Petrick et al. ................. | 604/525 |
| 2005/0085842 A1 * | 4/2005 | Eversull ................. | A61F 2/966 606/191 |
| 2007/0299424 A1 * | 12/2007 | Cumming et al. ............ | 604/527 |
| 2012/0277671 A1 * | 11/2012 | Fuentes ..................... | 604/95.04 |

* cited by examiner

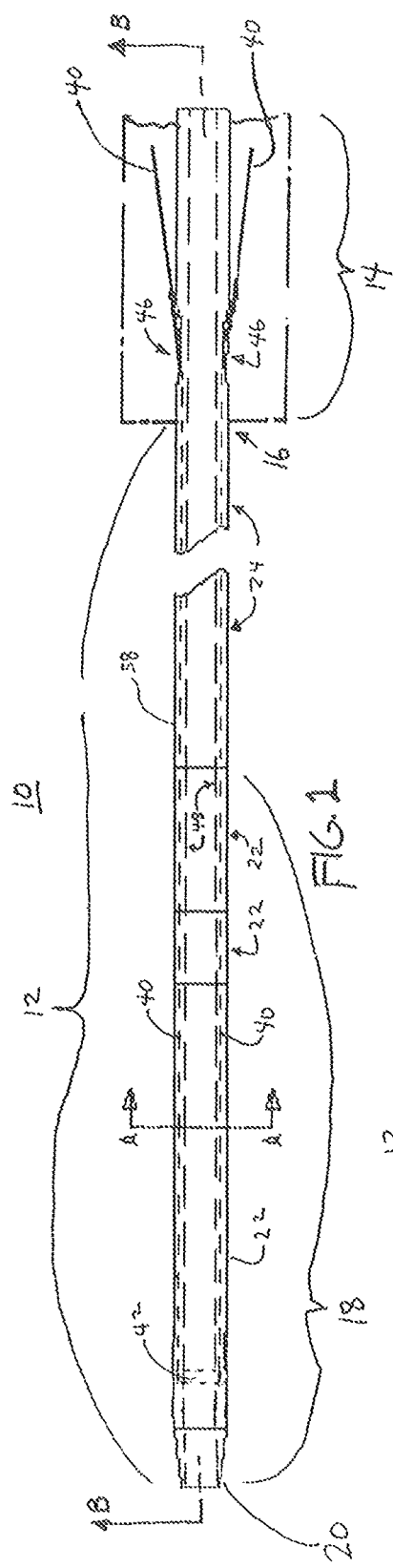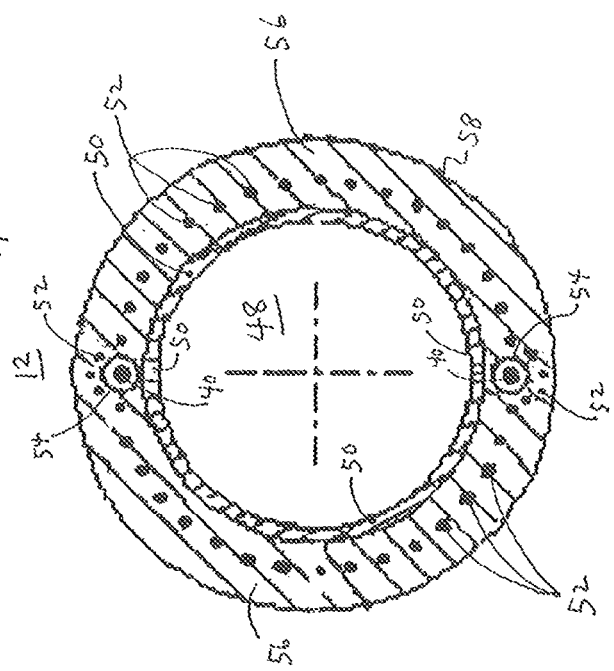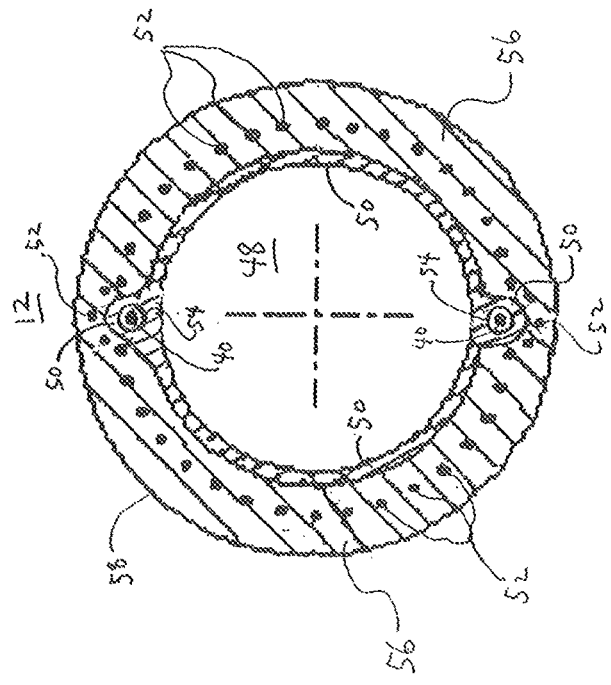

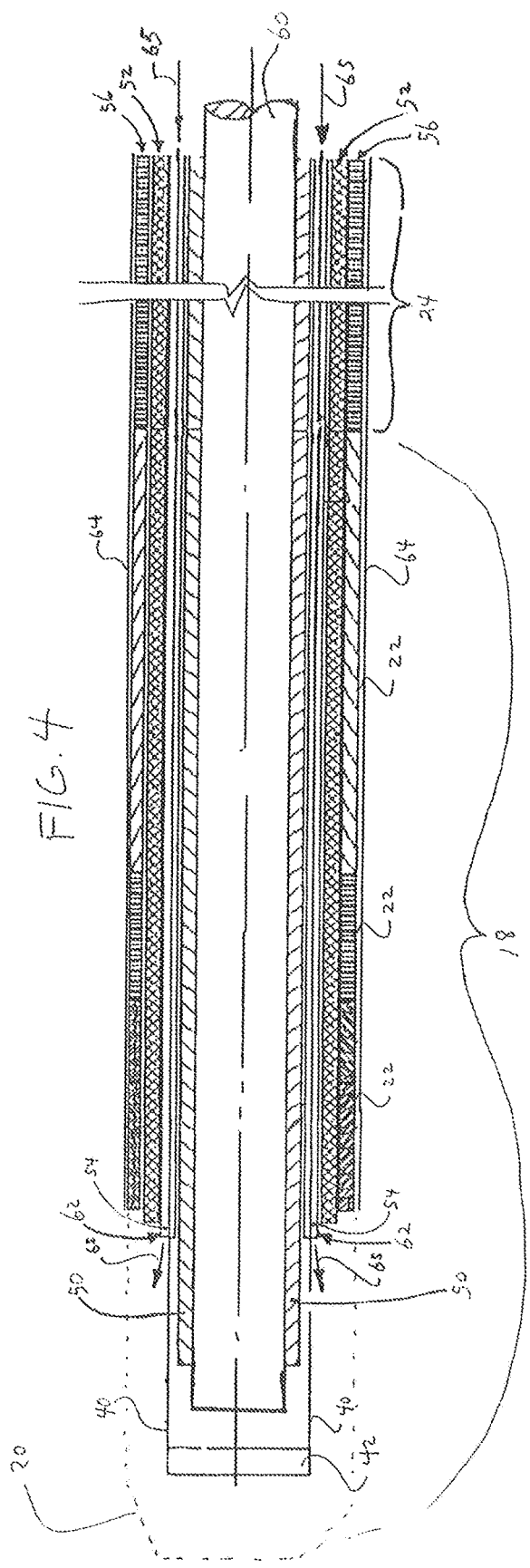

STEERABLE CATHETER AND METHODS OF MAKING THE SAME

CROSS-REFERENCE TO RELATED APPLICATIONS

This application is a continuation of U.S. application Ser. No. 11/033,098, filed 10 Jan. 2005 (the '098 application), now pending. The '098 application is hereby incorporated by reference as though fully set forth herein.

FIELD OF THE INVENTION

The present invention relates to catheters and sheaths and methods of making and using catheters and sheaths. More particularly, the present invention relates to the flexible tubular bodies of steerable catheters or sheaths and methods of making and using such bodies.

BACKGROUND OF THE INVENTION

A current method in the art used to manufacture flexible tubular bodies of steerable catheters or sheaths is to form the body on a mandrel using multiple layers: an inner liner intended to define the central lumen of the body; a layer of wire braid for reinforcing the body; and an outer thermoplastic jacket. The inner liner is pulled over the mandrel and tightened down. Deflection wires used to deflect the distal tip of the body are laid axially along the inner liner. The layer of wire braid is pulled or woven over the inner liner and deflection wires. After the wire braid is tightened down, the entire body is encased in a thermoplastic outer jacket. The outer jacket is then encased in heat-shrink material and heated. The heat causes the thermoplastic jacket layer to flow, which, when teamed with the pressure from the heat-shrink material, causes the thermoplastic outer jacket to impregnate the wire braid and embed the deflection wires. This consolidates the body into one integral unit.

Embedding the deflection wires in the flexible tubular body via the action of the thermoplastic polymer teamed with the heat-shrink material allows the deflection wires to create their own wire lumens. However, the deflection wires and the resulting wire lumens end up being approximately equal in diameter. This creates three related difficulties. First, significant deflection wire actuation friction is created between the walls of the wire lumens and the deflection wires as an operator attempts to deflect the body by moving the deflection wires. This actuation friction increases the difficulty in operating the deflection wires. Second, as the distal end of the body is deflected (bent) through the movement of the deflection wires, the wire braid embedded in the outer wall of the body is also flexed. As the wire braid flexes, the forces created can deform the central lumen. This can cause the wire braid to lock down on the deflection wires and the wire lumens. This greatly increases the deflection wire actuation friction and can prevent movement of the deflection wires as the wire lumens are deformed from a circular shape into an ovular shape. The third problem is that as the deflection wires are "locked down" in the bent body, the deflection wires and body loses the ability to spring back to the original shape as the force on the deflection wires from the operator at the proximal end is removed.

To overcome the aforementioned difficulties, U.S. Pat. No. 6,582,536 to Shimada, which issued Jun. 24, 2003, teaches creating flexible tubular bodies with lumens that are larger in diameter than the deflection wires to be received in the lumens. To achieve such an arrangement, a lumen defining wire is embedded in the outer thermoplastic jacket of the body to define a lumen. The lumen defining wire has a diameter that exceeds the diameter of the deflection wire to be received in the lumen. Once the oversized lumen is formed, the lumen defining wire is removed and the deflection wire is inserted into the oversized lumen.

The method taught in the Shimada patent helps reduce the deflection wire actuation friction and locking problems associated with deflection wires and their lumens. However, it does so at the cost of increased manufacturing complication, waste and, as a result, expense.

There is a need in the art for a less expensive method of manufacturing a flexible tubular body with deflection wires that generate less deflection wire actuation friction and are less likely to lock when the body is being deflected. There is also a need in the art for a flexible tubular body manufactured according to said method.

BRIEF SUMMARY OF THE INVENTION

The present invention, in one embodiment, is a method of manufacturing a flexible tubular body of a catheter, sheath or similar medical device. The method comprises pre-extruding an inner layer of the body from a thermoplastic polymer and then pulling the inner layer over a mandrel and tightening the layer down. If wire lumens were not integrally formed in the inner layer when pre-extruded, then two polymer spaghetti tubes, each with wire lumens, are laid 180 degrees apart axially along the outer surface of the inner layer. Deflection wires are then fed into the wire lumens. A cylindrical wire braid is woven or pulled over the inner layer (and the spaghetti tubes, as the case may be) and tightened down. The aforementioned components are then encased in an outer polymer layer. A heat-shrinkable tube is then placed over the outer layer. A pressurized fluid is injected into each wire lumen to maintain the internal diameter of each wire lumen at a diameter that is greater than the diameter of the deflection wire received in each wire lumen. Heat is then applied to the body and heat-shrinkable tube to cause the layers to laminate together. Once the newly laminated body has sufficiently cooled, the heat-shrinkable tube is removed from the body.

The present invention, in one embodiment, is a method of manufacturing a flexible tubular body of a catheter, sheath or similar medical device. The method comprises forming a wire lumen and injecting a fluid into the wire lumen. In one embodiment, a deflection wire is located in the wire lumen when the fluid is being injected.

In one embodiment, the fluid flows in a first end of the wire lumen and out an opposite end of the wire lumen. In one embodiment, the fluid is injected in a first end of the wire lumen, but the opposite end of the wire lumen is plugged so the fluid does not flow through the wire lumen.

In one embodiment, the fluid is a liquid. In another embodiment, the fluid is a gas. In one embodiment, the fluid is a gas at approximately 85 psig.

The present invention, in one embodiment, is a flexible tubular body of a catheter, sheath or similar medical device. The body comprises a deflection wire residing within a wire lumen having an inner diameter that exceeds the outer diameter of the deflection wire. During the manufacturing of the body, the wire lumen is injected with a fluid to prevent a reduction in the inner diameter.

In one embodiment, the body also includes an inner layer, an outer layer and a wire braid. The inner layer defines a central lumen. The outer layer surrounds the inner layer. The wire braid surrounds the inner layer and is impregnated by the outer layer.

In one embodiment, the wire lumen resides within at least a portion of the inner layer. For example, in such an embodiment, the wire lumen was pre-extruded with the inner layer during the manufacturing of the body. In another embodiment, the wire lumen resides within at least a portion of the outer layer. Specifically, the wire lumen is part of a pre-extruded spaghetti tube that was laid axially along an outer surface of the inner layer during the manufacturing of the body.

In one embodiment, the body also includes a fluid residue within wire lumen. The residue helps to lubricate the displacement of the deflection wire through the wire lumen.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is a side view of a steerable catheter or sheath employing the flexible tubular body of the present invention.

FIG. 2 is a lateral cross section of one embodiment of the flexible tubular body of the steerable catheter or sheath taken along section line AA in FIG. 1.

FIG. 3 is a lateral cross section of another embodiment of the flexible tubular body taken along section line AA in FIG. 1.

FIG. 4 is a longitudinal cross section of the body depicted in FIG. 2, as if taken along section line BB in FIG. 1, when being manufactured.

DETAILED DESCRIPTION

Figure 5:
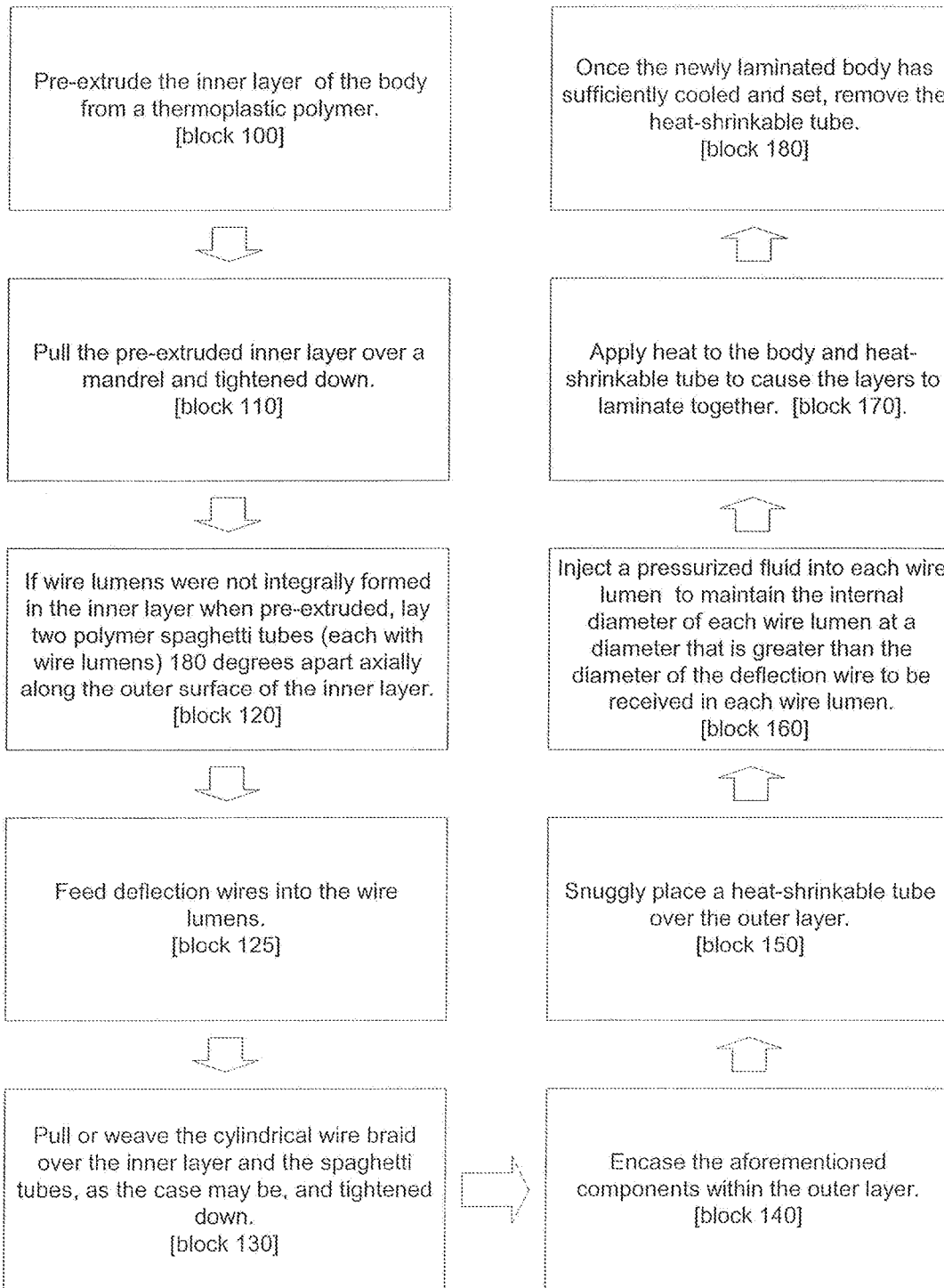
FIG. 5 is a flow chart outlining the method of manufacturing the body embodiments illustrated in FIGS. 2 and 3.

The present invention, in one embodiment, is a flexible tubular body for a steerable catheter, sheath or similar medical device that offers reduced deflection wire actuation friction and locking problems, but is less expensive and complicated to manufacture, as compared to prior art methods. During manufacturing of the flexible tubular body, oversized wire lumens are formed about deflection wires embedded in the wall of the body by injecting a pressurized fluid between the circumferential surfaces of the wire lumen and the deflection wire located therein.

For a discussion of a steerable catheter or sheath 10 employing the flexible tubular body 12 of the present invention, reference is now made to FIG. 1, which is a side view of the catheter or sheath 10. As shown in FIG. 1, the catheter or sheath 10 includes a generally tubular flexible body 12 and an actuation handle 14 coupled to a proximal end 16 of the body 12. A distal end 18 of the body 12 is adapted to deflect (i.e., bend) when actuated by the handle 14 and includes a soft tip 20 and a plurality of deflexing segments 22. The most proximal deflexing segment 22 is joined to a body segment 24 that extends to the proximal end 16.

As indicated by phantom lines in FIG. 1, a pair of deflection wires 40 extend through the body 12 from a pull ring 42 near the tip 20 until the wires 40 exit the body 12 via windows 46 in the actuator handle 14. The deflection wires 40 are coupled to an actuation mechanism in the handle 14 that causes the wires 40 to displace and, as a result, the distal end 18 to deflect.

As indicated by phantom lines in FIG. 1, in one embodiment, a central lumen 48 extends through the body 12 from the tip 20 to the handle 14. The central lumen 48 can be used to deliver medical fluids or equipment to a site within a patient.

As shown in FIG. 2, which is a lateral cross section of the flexible tubular body 12 taken along section line AA in FIG. 1, in one embodiment, the body 12 includes the central lumen 48, an inner layer 50, a cylindrical wire braid 52 employing wire with a flat or cylindrical cross-section, a pair of wire lumens 54 with deflection wires 40 received therein, an outer layer 56, and an outer circumferential surface 58. The outer layer 56 abuts against, and circumferentially encompasses, the inner layer 50, the wire braid 52 is embedded within the outer layer 56, and the wire lumens 54 are offset from each other about the central lumen 48 by approximately 180 degrees.

As illustrated in FIG. 2, in one embodiment, the wire lumens 54 exist within the outer layer 56. In another embodiment, as shown in FIG. 3, which is a cross section of the flexible tubular body 12 taken along section line AA in FIG. 1, the wire lumens 54 exist within the inner layer 50 such that, in one embodiment, the inner layer 50 is significantly thicker in the region of the wire lumens 54 to encompass the wire lumens 54 within the inner layer 50.

Regardless of the embodiment, as indicated in FIGS. 2 and 3, the inner diameter of the wire lumens 54 exceed the outer diameter of the deflection wires 40 received therein. The difference in diameters is sufficiently large that friction generated between the deflection wires 40 and the wire lumens 54 is minimized. Also, the likelihood that the deflection wires 40 will be locked up by the wire lumens 54 is minimized. However, the difference in diameters is still sufficiently small to allow the wire lumens 54 to adequately support the deflection wires 40 and prevent the wires 40 from buckling. In one embodiment, the difference between the inner diameter of a wire lumen 54 and the outer diameter of a deflection wire 40 therein is between approximately 0.002 inch and approximately 0.004 inch.

For a discussion regarding the manufacture of the above-discussed flexible tubular body 12, reference is now made to FIGS. 4 and 5. FIG. 4 is a longitudinal cross section of the body 12 depicted in FIG. 2 when being manufactured, as taken along section line BB in FIG. 1. FIG. 5 is a flow chart outlining the method of manufacturing the flexible tubular body embodiments illustrated in FIGS. 2 and 3.

As illustrated in FIGS. 4 and 5, in one embodiment, the inner layer 50 of the body 12 is pre-extruded from a thermoplastic polymer (e.g., polytetrafluoroethylene "PTFE", polyvinylidene fluoride "PVDF", polyetheretherketone "PEEK", etc.) [block 100]. The pre-extruded inner layer 50 is then pulled over a core rod or mandrel 60 and tightened down, as shown in FIG. 4 [block 110].

As illustrated in FIG. 4, in manufacturing the embodiment depicted in FIG. 2, two polymer spaghetti tubes 62 with wire lumens 54 for receiving the deflection wires 40 are laid 180 degrees apart axially along the outer surface of the inner layer 50 [block 120]. In one embodiment the spaghetti tubes 62 are pre-extruded from a polymer (e.g., polytetrafluoroethylene "PTFE", polyvinylidene fluoride "PVDF", polyetheretherketone "PEEK", etc.) In another embodiment the spaghetti tubes 62 are extruded as they are laid along the outer surface of the inner layer 50.

It should be noted, however, that the process of laying the spaghetti tubes 62 is not necessary when manufacturing the embodiment depicted in FIG. 3. This is because the wire lumens 54 of the embodiment depicted in FIG. 3 are extruded as an integral part of the inner layer 50 when the inner layer 50 is being extruded.

As shown in FIG. 4, in one embodiment, regardless of how the wire lumens 54 are formed, once the inner layer 50 exists on the mandrel 60, the deflection wires 40 are fed into the wire lumens 54 [block 125]. In another embodiment, the deflection wires 40 are fed into the wire lumens 54 later in the process, as discussed below.

As indicated in FIG. 4, the cylindrical wire braid 52 is pulled or woven over the inner layer 50 and, as the case may be, the spaghetti tubes 62. The wire braid 52 is then tightened down [block 130]. The entirety of the aforementioned components is then encased within the outer layer 56 [block 140]. For example, in one embodiment, the outer layer 56 is a pre-extruded layer that is pulled over the aforementioned components and tightened down. In another embodiment, the outer layer 56 is extruded over or sprayed onto the aforementioned components.

At the distal end 18 of the body 12, the outer layer 56 consists of the polymer material forming the deflexing segments 22 (e.g., polyether block amide "PEBA", polyvinylidene fluoride "PVDF", polyethylene terephthalate "PET", etc.). In one embodiment, the deflexing segments 22 are PEBA with durometer values that ranged between approximately 35 and approximately 55 on a type-D durometer. Along the body segment 24, the outer layer 56 consists of the polymer material forming the body segment 24 (e.g., polyether block amide "PEBA", polyvinylidene fluoride "PVDF", polyethylene terephthalate "PET", etc.). In one embodiment, the body segment 24 was PEBA with a durometer value of approximately 72 on a type-D durometer. Each polymer used for each deflexing segment 22 has a different deflexing compliance (i.e., durometer value) that is appropriate for the deflecting distal end 18 of a deflectable body 12 designed to deflect to specified curves.

As shown in FIG. 4, a heat-shrinkable tube 64 is snuggly placed over the outer layer 56 [block 150]. In one embodiment, the heat-shrinkable tube 64 is a polymeric material such as fluorinated ethylene-propylene copolymer "FEP", polytetrafluoroethylene "PTFE", or polyethylene terephthalate "PET". In one embodiment, the heat-shrinkable tube 64 has a shrink temperature ranging from approximately 190 degrees Celsius to approximately 220 degrees Celsius.

As indicated in FIG. 4, a pressurized fluid 65 (e.g., gases such as air, nitrogen, argon, carbon dioxide, etc. or liquids such as silicone gel fluid, silicone oil, etc.) is injected into each wire lumen 54 to maintain the internal diameter of each wire lumen 54 at a diameter that is greater than the diameter of the deflection wire 40 to be received in each wire lumen 54 [block 160]. In one embodiment, the pressurized fluid is injected into wire lumens 54 that are empty (i.e., the wire lumens 54 do not contain deflection wires 40 when being injected with the fluid). In another embodiment, as indicated in FIG. 4, the pressurized fluid is injected into wire lumens 54 that contains their respective deflection wires 40. In one embodiment, the fluid is maintained at a pressure of between approximately 50 psig and approximately 110 psig. In one embodiment, the fluid is air injected at approximately 85 psig.

In one embodiment, as indicated in FIG. 4, both ends of each wire lumen 54 are open such that the fluid 65 is injected in, for example, the proximal end of the wire lumen 54 and exits the distal end of the wire lumen 54. In other words, the fluid 65 flows through the wire lumen 54. In another embodiment, the distal end of the wire lumen 54 is sealed (e.g., by a UV adhesive) and the fluid 65 is injected in the proximal end such that the wire lumen 54 is pressurized, but the fluid 65 does not flow through the wire lumen 54.

Once the pressurized fluid is being injected into the wire lumens 54, heat is then applied to the body 12 [block 170]. The combination of the pressure from the heat-shrinkable tube 64 and the applied heat causes the aforementioned layers to laminate together, as illustrated in FIGS. 2 and 3. More specifically, the outer layer 56 melts and forcibly flows such that it impregnates the wire braid 52 and forms around and bounds with the inner layer 50 and, as the case may be, the spaghetti tubes 62. Because the wire lumens 54 are pressurized, their internal diameters are maintained and prevented from collapsing when the body 12 is subjected to the aforementioned pressure and heat.

In one embodiment, where the heat-shrinkable tube 64 is formed of FEP with a shrink temperature ranging from approximately 190 degrees Celsius to approximately 220 degrees Celsius, the body 12 and heat-shrinkable tube 64 are heated to within this temperature range. At this temperature range, the outer layer 56, which, in one embodiment, is formed of PEBA, melts and consolidates with the inner layer 50 and spaghetti tubes 62, which, in one embodiment, are formed of PTFE and chemically etched on their outer surfaces.

Once the newly laminated body 12 has sufficiently cooled and set, the heat-shrinkable tube 64 is removed from the body 12 [block 180]. If, as illustrated in FIG. 4, the wire lumens 54 were pressurized while containing their respective deflection wires 40, the body 12 is, generally speaking, ready to be formed into a catheter, sheath or similar medical device 10. The tip 20, shown in phantom lines in FIG. 4, and the handle 14 can then be added so the catheter or sheath 10 is formed as depicted in FIG. 1. If the wire lumens 54 were pressurized without containing their respective deflection wires 40, the deflection wires 40 must be inserted into the wire lumens 54 before the body 12 can be formed into a catheter or sheath 10.

In one embodiment, the polymeric material used for the inner layer 50 and, as the case may be, the spaghetti tubes 62, has a melting or softening point that is higher than those polymeric materials used for the outer layer 56 and the heat-shrinkable tube 64. In one embodiment, the polymeric materials used to form the inner and outer layers 50, 56 and, as the case may be, the spaghetti tubes 62, are chemically compatible such that they can be thermally bonded at the interfaces between the various polymeric materials.

In another embodiment, where the various polymeric materials are not necessarily chemically compatible such that they will thermally bond, the interfacing surfaces of the various materials will be subjected to physical or chemical surface modification to achieve reliable surface bonding. Physical surface modification includes plasma, corona, and laser surface treatments. Chemical surface modification refers to chemical etching methods.

Outright chemical compatibility between the various polymeric materials or surface modification to achieve reliable surface bonding is necessary to ensure that the body 12 is fully laminated during the lamination process into an integrated structure in the form of interfacial bonding by means of liquefying the outer layer 56. When heat is applied, the heat-shrinkable tube 64 starts to generate varying lamination pressure, which transfers inwards the thermal energy to liquefy the outer layer 56 during the lamination process.

To ensure that the outer layer 56 is completely liquefied during the lamination process, the shrink temperature of the heat-shrinkable tube 64 must be higher than the softening or melting temperature of the outer layer 56. The combination of the heat and pressure during lamination results in an integrated body 12 via polymer melt flow and interfacial bonding among all laminated components.

As indicated in FIG. 4, the mandrel 60 supports the central lumen 48 during the lamination process and prevents its collapse from the heat and pressure. As already discussed, the wire lumens 54 are pressurized via a fluid to prevent their collapse during the lamination process. The inflation fluid must be able to withstand the lamination temperature without thermally degrading, introducing contaminants into the polymeric material forming the wire lumens 54, or adversely impacting interfacial bonding. During lamination, the inflation pressure of the inflation fluid will act against the lamination pressure from the heat-shrinkable tube 64, keeping the wire lumens 54 open to their predefined dimensions.

Where the inflation fluid is lubricious (e.g., silicone gel fluid or oil), the fluid residue that remains in the wire lumen 54 helps to lubricate the displacement of the deflection wire 40. This decreases the friction generated between the deflection wire 40 and the wire lumen 54, thereby requiring less effort by a user to deflect the distal end 18 of the body 12. This also decreases the likelihood that the deflection wire 40 will lockup or bind within the wire lumen 54. To further decrease friction between the deflection wires 40 and the wire lumens 54, the deflection wires 40 can be coated with their own silicon or PTFE coatings.

Although the present invention has been described with reference to preferred embodiments, persons skilled in the art will recognize that changes may be made in form and detail without departing from the spirit and scope of the invention.

We claim:
1. An apparatus comprising:
   a flexible tubular body having a distal region and a proximal region, each of the distal region and the proximal region including an outer layer, an inner layer, at least two wire lumens, and a central lumen sized to receive a catheter or sheath, wherein the central lumen is defined by an inner surface of the inner layer; and
   at least two deflection wires,
   wherein each of the at least two wire lumens is defined by a respective one of a plurality of spaghetti tubes equidistantly placed about a circumference of an outer surface of the inner layer, the plurality of spaghetti tubes being positioned within at least a portion of the outer layer,
   wherein each of the at least two deflection wires is placed in a respective one of the at least two wire lumens, the at least two wire lumens each having an inner diameter that exceeds the outer diameter of its respective deflection wire,
   wherein each of the at least two wire lumens further contains a pressurized fluid to maintain the inner diameter of the at least two wire lumens, and
   wherein each of the at least two deflection wires extends through the flexible tubular body to a point in the distal region of the flexible tubular body.

2. An apparatus according to claim 1, wherein the inner layer comprises PTFE, the at least two wire lumens comprise PTFE, and the outer layer comprises PEBA.

3. An apparatus according to claim 1 further comprising a wire braid surrounding the inner layer and the at least two wire lumens.

4. An apparatus according to claim 3 wherein the wire braid is impregnated by the outer layer.

5. An apparatus according to claim 1 wherein the plurality of spaghetti tubes are thermally bonded to the inner layer.

6. An apparatus according to claim 1 wherein the outer layer is thermally bonded to the inner layer.

7. An apparatus according to claim 1 further comprising an actuation handle configured to be coupled to a proximal end of the flexible tubular body.

8. An apparatus according to claim 1 further comprising a pull ring.

9. An apparatus according to claim 8 wherein the at least two deflection wires are coupled to the pull ring.

10. An apparatus comprising:
    a shaft having a proximal end, a distal end, and a major lumen disposed therein extending between said proximal end and said distal end and configured to receive a medical device therein, said shaft further comprising;
    an inner layer extending along a length of said shaft and having an inner surface and an outer surface, said inner surface forming said major lumen;
    an outer layer extending along the length of said shaft adjacent said outer surface of said inner layer;
    two wire lumens extending along the length of said shaft; and
    two deflection wires extending through the shaft to a point within a distal region of the shaft,
    wherein the two wire lumens are defined by two spaghetti tubes on opposing sides of the outer surface of the inner layer, the two spaghetti tubes being positioned within at least a portion of the outer layer,
    wherein each of the two deflection wires is placed in a respective one of the two wire lumens, each of the two wire lumens having an inner diameter that exceeds the outer diameter of its respective deflection wire, and
    wherein each of the two wire lumens further includes a pressurized fluid to maintain the inner diameter of the two wire lumens.

11. An apparatus according to claim 10 further comprising a wire braid surrounding the inner layer and the two wire lumens.

12. An apparatus according to claim 10 wherein the two spaghetti tubes are thermally bonded to the inner layer.

13. An apparatus according to claim 10 wherein the outer layer is thermally bonded to the inner layer.

14. An apparatus according to claim 10 further comprising a pull ring.

15. An apparatus according to claim 10 further comprising an actuation handle configured to be coupled to a proximal end of the shaft.

16. A sheath having a central lumen to facilitate passage of a catheter, comprising:
    a flexible tubular body having a distal region and a proximal region, each of the distal region and the proximal region including an outer layer, an inner layer, at least two wire lumens, and a central lumen sized to receive a catheter or sheath, wherein the central lumen is defined by an inner surface of the inner layer; and
    at least two deflection wires,
    wherein each of the at least two wire lumens is defined by a respective one of a plurality of spaghetti tubes equidistantly placed about a circumference of the outer surface of the inner layer, the plurality of spaghetti tubes thermally bonded to the outer surface of the inner layer, wherein each of the at least two deflection wires is placed in a respective one of the at least two wire lumens, the at least two wire lumens each having an inner diameter that exceeds the outer diameter of its respective deflection wire, wherein each of the at least two wire lumens further includes a pressurized fluid to maintain the inner diameter of the at least two wire lumens, and wherein each of the at least two deflection wires terminates at a point within the distal region of the flexible tubular body.

17. A sheath according to claim 16 further comprising an actuation handle configured to be coupled to a proximal end of the flexible tubular body.

18. A sheath according to claim 16 further comprising a wire braid surrounding the inner layer and the at least two wire lumens.

19. A sheath according to claim 16 wherein the outer layer is thermally bonded to the inner layer.

20. A sheath according to claim 16 further comprising a pull ring.

* * * * *